United States Patent
Poletti

(10) Patent No.: US 8,685,907 B2
(45) Date of Patent: Apr. 1, 2014

(54) MAKEUP REMOVER GEL CONTAINING JOJOBA OIL

(75) Inventor: Mickael Poletti, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/699,338

(22) Filed: Feb. 3, 2010

(65) Prior Publication Data

US 2010/0210498 A1 Aug. 19, 2010

Related U.S. Application Data

(60) Provisional application No. 61/153,987, filed on Feb. 20, 2009.

(30) Foreign Application Priority Data

Feb. 13, 2009 (FR) .................... 09 50931

(51) Int. Cl.
*A61K 8/00* (2006.01)

(52) U.S. Cl.
USPC ........... 510/130; 510/134; 510/136; 424/70.1

(58) Field of Classification Search
None
See application file for complete search history.

(56) References Cited

U.S. PATENT DOCUMENTS 5,603,940 A * 2/1997 Candau et al. ............... 424/401

FOREIGN PATENT DOCUMENTS

| EP | 1 103 250 | 5/2001 |
| JP | 05-229916 | 9/1993 |

OTHER PUBLICATIONS

Database Caplus (Online), Chemical Abstracts Service, Columbus, Ohio, US; Jun. 22, 1985; "Transparent Cleansing Gel Compositions for the Skin," XP002556997, Database Accession No. 1985:600703 and JP 60 115509, Jun. 22, 1985.

Green Herbal Remedies: "Jojoba Oil for Complete Winter Moisturizing Needs," Online, Dec. 15, 2008; XP002557192, URL; http://www.greenherbalremedies.com/blog/jojoba-oil-for-complete-winter-moisturising-needs/>, Nov. 23, 2009.

Anna Cristofaro:, "Uses of Jojoba Oil," Online, Feb. 21, 2007, XP002556995, URL:http://beauty-treatments.suite101.com/article.cfm/uses_of_jojoba_oil>, Nov. 23, 2009.

* cited by examiner

*Primary Examiner* — Necholus Ogden, Jr.
(74) *Attorney, Agent, or Firm* — Oblon, Spivak, McClelland, Maier & Neustadt, L.L.P.

(57) ABSTRACT

Composition containing an aqueous phase, at least 35% by weight of jojoba oil relative to the total weight of the composition, and at least one sucrose fatty acid ester. The composition is preferably in the form of a gel. It may be used, in particular, for removing makeup from the skin and/or the eye area and/or the lips.

25 Claims, No Drawings

MAKEUP REMOVER GEL CONTAINING JOJOBA OIL

REFERENCE TO PRIOR APPLICATIONS

This application claims priority to U.S. provisional application Ser. No. 61/153,987, filed Feb. 20, 2009; and to French patent application 09 50931, filed Feb. 13, 2009, both incorporated herein by reference.

FIELD OF THE INVENTION

The invention relates to a composition comprising jojoba oil and a sucrose fatty acid ester emulsifier, and to its use in the cosmetics field, especially for removing makeup from and/or cleansing keratin materials.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Modern makeup technologies are increasingly innovative and highly performing, and there are more and more users of makeup products who use long-lasting products such as non-transfer foundations, long-lasting lipsticks, waterproof mascaras or two-step mascaras (involving application first of a base then of a topcoat of mascara).

However, these types of product are more difficult to remove than conventional makeup products, and consequently there exists a need for makeup remover products that combine high performance with practicality in use and which are kind to the skin while having good cosmetic qualities (comfort in use, softness).

Moreover, for several years the cosmetics market has been marked by a very great demand for formulations containing ingredients of natural origin. Consumers desire formulations that are free of chemical substances, preferring instead ingredients of natural origin, renowned for their better tolerance and affinity for the skin, and which are more environmentally friendly.

In view of this background, the inventors have addressed the need to have a makeup remover product comprising ingredients of natural origin that are very innocuous with respect to keratin materials, while nevertheless having the required properties for products that combine high performance for all types of makeup (conventional and long-lasting), with practicality in use and comfort.

DETAILED DESCRIPTION OF THE PREFERRED EMBODIMENTS

The inventors have discovered that the combination of a sucrose fatty acid ester surfactant with a particular plant oil makes it possible to achieve the above objectives.

One subject of the present invention is therefore a composition comprising an aqueous phase, at least 35% by weight of jojoba oil relative to the total weight of the composition, and at least one sucrose fatty acid ester.

The composition according to the invention has the advantage of being capable of being gelled, and therefore easy to use, while being comfortable and enabling good removal of any type of makeup, in particular waterproof or long-lasting makeup. It also exhibits good stability.

The composition according to the invention is preferably in gelled form, in particular in the form of a gel of the oil-in-water emulsion type, comprising a fatty phase dispersed in an aqueous phase. The term "gelled" is understood to mean the fact that the composition does not run, that is to say that it has a certain viscosity. Its viscosity may range, for example, from 5 to 190 poise (0.5 to 19 Pa·S), preferably from 5 to 150 poise (0.5 to 15 Pa·S) and better still from 10 to 120 poise (1 to 12 Pa·S), the viscosity being measured using a Rheomat 180 viscometer at a shear rate of 200 $s^{-1}$ and at 25° C. Viscosities of 0.5, 1, 2, 3, 4, 5, 6, 7, 8, 9, 10, 11, 12, 13, 14, 15, 16, 17, 18, and 19 Pa·s are included, as are all values and subranges between the ranges stated above.

The composition according to the invention is preferably intended for topical application and therefore preferably contains a physiologically acceptable medium. The expression "physiologically acceptable medium" is understood here to mean a medium that is compatible with keratin materials such as the skin, mucous membranes, the scalp, the eyes and/or keratin fibres such as the eyelashes or the hair.

Sucrose Fatty Acid Ester

According to the present invention, the sucrose fatty acid ester is preferably chosen from the esters derived from the reaction of sucrose(s) (saccharose) and fatty acid(s) comprising from 10 to 24 carbon atoms, preferably from 12 to 20 carbon atoms, better still from 12 to 18 carbon atoms and even better still from 12 to 16 carbon atoms.

The fatty acids comprising from 10 to 24 carbon atoms may be linear or branched, saturated or unsaturated.

The fatty acids may be chosen from oleic acid, lauric acid, palmitic acid, myristic acid, stearic acid, linoleic acid, capric acid or mixtures thereof.

According to one embodiment, the sucrose fatty acid ester is chosen from the esters derived from the reaction of sucrose and of fatty acid comprising from 12 to 18 carbon atoms, preferably from 12 to 16 carbon atoms, for instance lauric acid and/or palmitic acid, such as for example sucrose laurate, sucrose palmitate or a mixture thereof.

The sucrose fatty acid esters may be chosen from monoesters, diesters, triesters and tetraesters, polyesters and mixtures thereof. Use is preferably made of esters having a low degree of esterification such as for example sucrose fatty acid monomers, diesters or triesters, or a mixture thereof. The sucrose fatty acid ester may be in the form of a mixture of esters having a low degree of esterification such as for example a mixture of monoester and diester or a mixture of monoester, diester and triester.

In the case where a mixture of sucrose fatty acid esters is used, a mixture in which the esters having a low degree of esterification, in particular the monoesters, are predominant and represent, for example, at least 50%, preferably at least 60% by weight of the mixture of sucrose fatty acid esters is preferred.

Use may in particular be made of a mixture of sucrose esters of fatty acids comprising from 12 to 16 carbon atoms, in particular a mixture of monoesters, diesters and triesters of lauric acid or of palmitic acid, said mixture possibly comprising, as a minority (in an amount less than or equal to 40% by weight relative to the weight of the mixture of sucrose fatty acid esters), sucrose fatty acid esters in which the fatty acid comprises more than 16 carbon atoms.

Preferably, the sucrose fatty acid ester used in the present invention has an HLB greater than or equal to 10, preferably greater than or equal to 12.

As is well known, HLB (hydrophilic-lipophilic balance) is the balance between the size and strength of the hydrophilic group and the size and strength of the lipophilic group of the surfactant.

The HLB value according to Griffin is defined in J. Soc. Cosm. Chem. 1954 (volume 5), pages 249-256.

As examples of sucrose fatty acid esters or mixtures of esters mention may be made of:

Surfhope SE COSME C-1416, having an HLB of 16, which is a sucrose myristate comprising around 80% of monoester, the rest of the mixture being composed of diesters and triesters;

Surfhope SE COSME C-1216, the INCI name of which is sucrose laurate, having an HLB equal to 16 and comprising 75 to 900 of monoester, the rest of the mixture being composed of diesters and triesters;

Surfhope SE COSME C-1215L, the INCI name of which is sucrose laurate, having an HLB equal to 15, comprising around 70% of monoesters, the rest of the mixture being composed of diesters and other polyesters; and Surfhope SE COSME C-1616, having an HLB of 16, which is a mixture of saccharose esters of palmitic and/or stearic acids (INCI name sucrose palmitate), comprising from 75 to 90% of monoester, the rest of the mixture being composed of diesters and triesters, and possibly comprising sucrose stearate and sucrose palmitate stearate.

Mention may also be made of the ester bearing the INCI name sucrose laurate, sold by Dai-Ichi Seiyaku under the reference DK Ester S-L18A, having an HLB equal to 17 and comprising 70% of monoesters and 30% of diesters and triesters.

As examples of sucrose fatty acid esters or mixtures of esters mention may also be made of:

the products sold under the names F160, F140, F110, F90, F70, SL40 by Crodesta, respectively denoting sucrose palmito-stearates formed from 73% of monomester and 27% of diester and triester, from 61% of monoester and 39% of diester, triester and tetraester, from 52% of monoester and 48% of diester, triester and tetraester, from 45% of monoester and 55% of diester, triester and tetraester, from 39% of monoester and 61% of diester, triester and tetraester, and sucrose monolaurate;

the products sold under the name Ryoto Sugar Esters, for example referenced B370 and corresponding to saccharose behenate formed from 20% of monoester and 80% of diester/triester/polyester; and the sucrose mono-dipalmito-stearate sold by Goldschmidt under the name Tegosoft PSE.

The amount of sucrose fatty acid ester(s) is not limited and may range, for example, from 0.1 to 20% by weight, preferably from 0.5 to 15% by weight, better still from 1 to 15% by weight, even better still from 2 to 10% by weight relative to the total weight of the composition.

According to one embodiment, the composition according to the invention may comprise, besides the sucrose fatty acid ester, one or more additional surfactants chosen from anionic, non-ionic or amphoteric surfactants, and mixtures thereof, in particular non-ionic surfactants, but preferably only insofar as the presence of these surfactants is not detrimental to the comfort (innocuousness) of the composition.

The additional surfactants that may be used in the composition according to the invention are preferably surfactants of natural origin, included in which are the compounds which may be present in nature and which are reproduced by chemical synthesis, they may especially be chosen from soaps (salts of fatty acids), derivatives of soybean oil, derivatives of lactic acid, amino acids, acylamino acids, salts thereof, alkylpolyglucosides (APG), hydrophobicized gums and mixtures thereof.

According to another embodiment, the sucrose fatty acid ester or esters constitute the main surfactant system of the composition.

The expression "main surfactant system" is understood to mean a system which, in its absence, does not result in the formation of a stable composition. The term "stable" is understood to mean a composition which, after having been placed in an oven at 45° C. for two months, does not exhibit, after return to ambient temperature, phase separation of the fatty and aqueous phases, or leaching of the fatty phase at the surface.

According to another embodiment, the sucrose fatty acid ester or esters constitute the only surfactant system of the composition.

The term "only" is understood to mean any optional additional surfactant system is present in an amount that does not exceed 1%, and preferably that does not exceed 0.5%. More preferably, the term "only" denotes a total absence of any other surfactant system.

Aqueous Phase

The composition according to the invention comprises an aqueous phase comprising water and/or hydrophilic solvents such as polyols.

The water is preferably present in an amount less than or equal to 20% by weight relative to the total weight of the composition, preferably less than or equal to 15% by weight and better still less than or equal to 10% by weight. The amount of water in the composition may range, for example, from 0.5 to 20% by weight, preferably from 0.6 to 15% by weight, better still from 0.6 to 13% by weight, even better still from 1 to 10% by weight and even better still from 3 to 10% by weight relative to the total weight of the composition.

The water used in the composition of the invention may be pure demineralized water or else mineral water and/or thermal spring water and/or sea water; in other words, the water of the composition may be composed in part or entirely of a water selected from mineral waters, thermal spring waters, sea waters and mixtures thereof. Generally speaking, a mineral water is suitable for consumption, which is not always the case with a thermal spring water. Each of these waters contains, among other constituents, solubilized minerals and/or trace elements. The use of these waters for specific treatment purposes, depending on the specific minerals and trace elements which they contain, is known, such treatments including the moisturizing and desensitizing of the skin or the treatment of certain dermatoses. The terms "mineral waters" or "thermal spring waters" will be used to denote not only natural mineral or thermal spring waters but also natural mineral or thermal spring waters which have been enriched with additional mineral constituents and/or trace elements, and also aqueous mineral solutions and/or aqueous solutions containing trace elements that have been prepared from purified water (demineralized or distilled water).

A natural thermal spring or mineral water used according to the invention may be selected, for example, from Vittel water, Vichy basin water, Uriage water, La Roche Posay water, Bourboule water, Enghien-les-Bains water, Saint Gervais-les-Bains water, Néris-les-Bains water, Allevar-les-Bains water, Digne water, Maizières water, Neyrac-les-Bains water, Lons-le-Saunier water, Eaux Bonnes water, Rochefort water, Saint Christau water, Fumades water, Tercis-les-Bains water and Avene water.

The aqueous phase of the composition of the invention may comprise one or more polyols. Polyols which can be used in the composition according to the invention include, in particular, glycerol, propylene glycol, butylene glycol, hexylene glycol, polyethylene glycols such as PEG-8, dipropylene glycol and mixtures thereof. According to one preferred embodiment of the invention, the polyol is glycerol, which gives better comfort on application. The glycerol can be admixed with other polyols, provided that the qualities of the composition are maintained.

The amount of polyol(s) may range for example from 0.5% to 15% by weight, preferably from 0.5% to 10% by weight, better still from 1% to 10% by weight, even better still from 2% to 10% by weight and even better still from 2% to 8% by weight relative to the total weight of the composition.

The composition may comprise a hydrophilic gelling agent, preferably chosen from gelling agents of natural origin, in particular of plant origin, or polysaccharides of biotechnological origin (for example xanthan gum).

This plant-derived polysaccharide may, where appropriate, be chemically modified to promote its hydrophilic valency, as is the case for cellulose derivatives, in particular hydroxyalkyl celluloses (e.g.: hydroxyethyl cellulose).

As examples of polysaccharides of plant origin that may be used according to the invention, mention may be made especially of:

a) algal extracts, such as alginates, carrageenans and agars, and mixtures thereof. Examples of carrageenans that may be mentioned include Satiagum UTC30® and UTC10® from Degussa; an alginate that may be mentioned is the sodium alginate sold under the name Kelcosol® by ISP;

b) gums, such as guar gum and non-ionic derivatives thereof (hydroxypropyl guar), gum arabic, konjac gum or mannan gum, gum tragacanth, ghatti gum, karaya gum or locust bean gum; examples that may be mentioned include the guar gum sold under the name Jaguar HP105® by Rhodia; the mannan and Konjac Gum® (1% glucomannan) sold by GfN;

c) modified or unmodified starches, such as those obtained, for example, from cereals, for instance wheat, corn or rice, from legumes, for instance blonde pea, from tubers, for instance potato or cassava, and tapioca starches; dextrins, such as corn dextrins; examples that may especially be mentioned include the rice starch Remy DR I® sold by Remy; the corn starch B® from Roquette; the potato starch modified with 2-chloroethylaminodipropionic acid neutralized with sodium hydroxide, sold under the name Structure Solanace® by National Starch; the native tapioca starch powder sold under the name Tapioca Pure® by National Starch;

d) dextrins, such as the dextrin extracted from corn under the name Index® from National Starch;

e) celluloses and derivatives thereof, in particular alkyl celluloses, hydroxyalkyl celluloses; mention may be made especially of methyl celluloses, hydroxyalkyl celluloses, ethylhydroxyethyl celluloses and carboxymethyl celluloses. Examples that may be mentioned include the cetyl hydroxyethyl celluloses under the names Polysurf 67CS® and Natrosol Plus 330® from Aqualon;

and mixtures thereof.

According to one embodiment, the composition according to the invention comprises less than 1.5% by weight of synthetic gelling or thickening polymers, preferably less than 1%, better still less than 0.5%, or even less than 0.2% by weight. It may be completely free of synthetic gelling or thickening polymers.

Such synthetic polymers are, for example, acrylic polymers (Carbopol family), acrylic/alkylacrylate copolymers or (co)polymers based on 2-acrylamido-2-methylpropanesulphonic acid (for example the polymers sold under the names Pemulen, Sepigel, Simulgel or Aristoflex).

Fatty Phase

The fatty phase of the composition according to the invention comprises all the liposoluble or lipodispersible compounds present in the composition, including the fatty substances that are liquid at ambient temperature (25° C.) or oils (that form the oily phase), the fatty substances that are solid at ambient temperature such as waxes, or else pasty compounds, fatty alcohols or fatty acids.

Jojoba Oil

Jojoba oil is present in the composition in an amount greater than or equal to 35% by weight, preferably greater than or equal to 40% by weight relative to the total weight of the composition, preferably greater than or equal to 50% by weight, better still greater than or equal to 60% by weight and even better still greater than or equal to 70% by weight relative to the total weight of the composition. The amount of jojoba oil may range, in particular, from 35 to 90% by weight, preferably from 40 to 85%, better still from 45 to 80% by weight relative to the total weight of the composition.

The composition according to the invention may comprise, besides jojoba oil, one or more additional oils, in particular an additional oil of plant origin.

When the composition comprises an additional oil, the additional oil is preferably present in an amount less than the amount of jojoba oil.

In particular, the jojoba oil is present in an amount of at least 50% by weight relative to the total weight of the oily phase of the composition, preferably at least 60% by weight and better still at least 70% by weight, it may range up to 100% by weight of the oily phase.

The additional oil may be present in an amount ranging from 0.5 to 40% by weight relative to the total weight of the composition, preferably from 0.5 to 30% by weight and better still from 1 to 20% by weight.

Oils which can be used in the composition of the invention may include, for example:

hydrocarbon oils of animal origin, such as perhydrosqualene;

hydrocarbon oils of plant origin, such as liquid triglycerides of fatty acids containing 4 to 30 carbon atoms, such as triglycerides of heptanoic or octanoic acids or else, for example, sunflower oil, corn oil, soybean oil, marrow oil, grapeseed oil, sesame oil, hazelnut oil, apricot oil, macadamia oil, arara oil, coriander oil, castor oil, avocado oil, caprylic/capric acid triglycerides such as those sold by Stearineries Dubois or those sold under the names Miglyol 810, 812 and 818 by Dynamit Nobel and shea butter oil;

synthetic esters and ethers, especially of fatty acids, such as oils of formulae $R^1COOR^2$ and $R^1OR^2$ in which $R^1$ represents the residue of a fatty acid or fatty alcohol containing 8 to 29 carbon atoms and $R^2$ represents a branched or unbranched hydrocarbon chain containing 3 to 30 carbon atoms, such as, for example, purcellin oil, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters, such as propylene glycol dioctanoate, neopentyl glycol diheptanoate and diethylene glycol diisononanoate; and pentaerythritol esters such as pentaerythrityl tetraisostearate;

linear or branched hydrocarbons of mineral or synthetic origin, such as volatile or non-volatile liquid paraffins and their derivatives, petroleum jelly, polydecenes, isohexadecane, isododecane, hydrogenated polyisobutene such as Parléam® oil;

silicone oils, such as volatile or non-volatile polydimethylsiloxanes (PDMS), containing a linear or cyclic silicone chain, which are liquid or pasty at ambient temperature, especially volatile silicone oils, in particular cyclopolydimethylsiloxanes (cyclomethicones) such as cyclohexadimethylsiloxane and cyclopentadimethylsiloxane; polydimethylsiloxanes containing alkyl, alkoxy or phenyl groups that are pendent or at the silicone chain end, said groups having 2 to 24 carbon atoms; phenyl silicones such as phenyltrimethicones, phenyldimethicones, phenyltrimethylsiloxydiphenylsiloxanes, diphenyldimethicones, diphenyldimethyldiphenyl-trisiloxanes, 2-phenylethyl trimethylsiloxysilicates, and polymethylphenylsiloxanes;

and mixtures thereof.

Mention may in particular be made of the oils chosen from:

the esters derived from the reaction of at least one fatty acid comprising at least 6 carbon atoms, preferably from 6 to 26 carbon atoms and better still from 6 to 20 carbon atoms, even better still from 6 to 16 carbon atoms and of at least one alcohol comprising from 1 to 17 carbon atoms and better still from 3 to 15 carbon atoms; mention may especially be made of isopropyl myristate, isopropyl palmitate, 2-ethylhexyl caprate/caprylate (or octyl caprate/caprylate), 2-ethylhexyl palmitate, isostearyl neopentanoate, isononyl isononanoate, hexyl laurate, the esters of lactic acid and of fatty alcohols comprising 12 or 13 carbon atoms, dicaprylyl carbonate such as that which is sold under the name CETIOL CC by Cognis;

fatty acid ethers comprising from 6 to 20 carbon atoms such as dicaprylyl ether (Cetiol OE from Cognis);

glyceryl ethers comprising from 6 to 12 carbon atoms such as 2-ethylhexyl glyceryl ether (INCI name: ethylhexyl glycerin) such as Sensiva SC 50 from Schulke & Mayr GmbH;

volatile linear alkanes, advantageously from plant origin, comprising from 7 to 17 carbon atoms, in particular from 9 to 15 carbon atoms, and more particularly from 11 to 13 carbon atoms. As examples of volatile linear alkanes suitable for the invention, mention may be made of those described in the patent application by Cognis WO 2007/068371. As examples of volatile linear alkanes suitable for the invention, mention may be made of n-nonane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$), n-hexadecane ($C_{16}$) and n-heptadecane ($C_{17}$) and mixtures thereof. According to one embodiment, use will be made of a mixture of undecane ($C_{11}$) and of tridecane ($C_{13}$) prepared according to examples 1 and 2 of the WO2008/155059 application by Cognis;

According to one embodiment, use will be made of n-dodecane ($C_{12}$) or n-tetradecane ($C_{14}$) sold by SASOL respectively under the trade names PARAFOL 12-97 and PARAFOL 14-97, and mixtures thereof.

Preferably, the additional oil contains/is chosen from plant oils, volatile linear alkanes, advantageously of plant origin, fatty acid esters and ethers, and mixtures thereof.

According to one advantageous embodiment, the composition according to the invention comprises less than 5% and preferably less than 1% of mineral oils. Preferably, it comprises only oils of plant origin.

The compositions of the invention may, in addition, contain adjuvants which are commonplace in the cosmetics field, such as antioxidants, preservatives, fragrances, fragrance peptizing agents, colourants, fillers and hydrophilic or lipophilic active agents. The nature of the adjuvants and the amounts thereof should preferably be such that they do not modify the properties of the composition according to the invention. The amounts of these adjuvants include those conventionally used in the cosmetics field and are, for example, from 0.001 to 10% of the total weight of the composition.

As active agents that can be used in the composition of the invention, mention may be made, for example, of soothing agents such as allantoin and bisabolol; floral waters such as lime water or cornflower water; glycyrrhetinic acid and its salts; antibacterial agents such as octipirox, triclosan and triclocarban; essential oils; vitamins such as for example retinol (vitamin A), ascorbic acid (vitamin C), tocopherol (vitamin E), niacinamide (vitamin PP or B3), panthenol (vitamin B5) and derivatives thereof such as for example the esters of these vitamins (palmitate, acetate, propionate), magnesium ascorbyl phosphate, glycosylated vitamin C or glucopyranosyl ascorbic acid (ascorbyl glucoside); coenzymes such as coenzyme Q10 or ubiquinone and coenzyme R or biotin; protein hydrolysates; plant extracts and especially plankton extracts; and mixtures thereof.

Of course, a person skilled in the art will be sure to choose the optional additive or additives to be added to the composition according to the invention so that the advantageous properties intrinsically linked to the composition according to the invention are not, or are not substantially, adversely affected by the envisaged addition.

As fillers, mention may be made of mineral fillers such as talc or magnesium silicate (particle size: 5 microns) sold under the name Luzenac 15 M00® by Luzenac, kaolin or aluminium silicate such as for example that sold under the name Kaolin Supreme® by Imerys, or organic fillers such as starch for instance the product sold under the name Maize Starch B® by Roquette, nylon microspheres such as those sold under the name Orgasol 2002 UD NAT COS® by Atochem, expanded microspheres based on a copolymer of vinylidene chloride/acrylonitrile/methacrylonitrile enclosing isobutane such as those sold under the name Expancel 551 DE® by Expancel. Fibres, such as for example nylon fibres (Polyamide 0.9 DTEX 0.3 mm, sold by Etablissements Paul Bonte) or cellulose or "Rayon" fibres (Rayon Flock RCISE NOOO3 MO4® sold by Claremont Flock Corporation) may also be added to the composition of the invention.

According to one particular embodiment of the invention, the composition according to the invention contains, as fillers, exfoliating particles that will enable the skin to be scrubbed. As exfoliating particles, it is possible to use exfoliating or scrubbing particles of mineral, plant or organic origin. Thus, it is possible to use, for example, polyethylene beads or powder, such as those sold under the name Microthene MN 727 or Microthene MN 710-20 by Equistar or such as the powder sold under the name Gotalene 120 Colourless 2 by Dupont; nylon particles such as those sold by Arkema under the name Orgasol 2002 EXD NAT COS; fibres such as polyamide fibres, for instance those sold by Utexbel under the name Pulpe Polyamide 12185 Taille 0.3 MM [Polyamide Pulp 12185 size 0.3 mm]; polyvinyl chloride powder; pumice (INCI name: pumice) such as the pumice 3/B from Eyraud; the ground shells of fruit stones such as apricot kernel or nut shell homogenates; sawdust; glass beads; alumina (aluminium oxide) (INCI name: Alumina) such as the product sold under the name Dermagrain 900 by Marketech International; sugar crystals; beads which melt on application to the skin, such as for example spheres based on mannitol and cellulose sold under the names Unispheres by Induchem, agar-based capsules sold under the names Primsponge by Cognis, and spheres based on jojoba esters sold under the names Floraspheres by Floratech; and mixtures thereof.

The compositions according to the invention may especially constitute products for cleansing or removing makeup from keratin materials such as the skin (body, face, eyes, scalp) and/or keratin fibres.

Another subject of the invention is a method for cleansing or removing makeup from keratin materials such as the skin, including the scalp, keratin fibres such as eyelashes or the hair, and/or lips, characterized by the fact that a cosmetic composition as defined above is applied to said keratin fibres.

Another subject of the invention comprises the cosmetic use of the composition as defined above, as products for cleansing and/or removing makeup from keratin materials.

Another subject of the invention comprises a cosmetic method of cleansing keratin materials, characterized by the fact that the composition of the invention is applied to keratin materials, in the presence of water, and that the deposition formed and the dirt residues are removed by rinsing with water.

In the case of cleaning the face, the composition according to the invention may constitute a mask which is rinsed off after a leave-on of one to three minutes, for example.

The following examples are given by way of illustration of the invention and are not of a limiting nature. All the amounts are given as percentages by weight relative to the total weight of the composition. The names of the compounds are indicated, depending on the case, as chemical names or as INCI names:

Examples 1 to 4

|  | Ex 1 outside the invention | Ex 2 Invention | Ex 3 Invention | Ex 4 Invention |
| --- | --- | --- | --- | --- |
| Phase A |  |  |  |  |
| Sucrose Palmitate (Surfhope SE COSME C-1616 from Mitsubishi Kagaku Foods Corp.) | 3 | 3 | 3 | 3 |
| Sucrose Laurate (Surfhope SE COSME C-1216 from Mitsubishi Kagaku Foods Corp.) | 3 | 3 | 3 | 3 |
| Glycerol | 10 | 10 | 10 | 10 |
| Water | 5 | 5 | 5 | 5 |
| Potassium sorbate | 0.3 | 0.3 | 0.3 | 0.3 |
| Phase B |  |  |  |  |
| Organic jojoba oil (from Fytosan) | 30 | 46 | 62 | 76 |
| Olive oil | 48 | 32 | 16 | — |
| Phase C |  |  |  |  |
| Citric acid | qs for pH 5.3 ± 0.3 | qs for pH 5.3 ± 0.3 | qs for pH 5.3 ± 0.3 | qs for pH 5.3 ± 0.3 |
| Water | qs for 100 | qs for 100 | qs for 100 | qs for 100 |

Procedure:

The sucrose esters and the glycerol are mixed, then the other compounds of phase A are added and the assembly is heated at 75-80° C.

The compounds from phase B are mixed and heated at 75-80° C., then phase B is added to phase A with gentle stirring and left to cool while continuing this stirring. Phase C is added when the mixture has come back down to 35-40° C.

Evaluation of the In Vivo Makeup Removing Efficacy:

The makeup removing efficacy of each composition from examples 1 to 4 is evaluated on five individuals according to the following protocol:

On each individual, four areas of 3×3 cm are delimited on the forearm and 0.05 g of Infallible 300 foundation (L'Oréal Paris) is applied using a finger to each area of 3×3 cm, then is left to dry for 30 minutes.

0.3 g of each composition is applied to an area using a finger for ten seconds, then the forearm is then passed under a trickle of water at a set temperature and flow rate.

Once the mixtures are emulsified and rinsed, each model evaluates and classifies the four compositions tested according to their level of makeup removing efficacy according to a 4-point scale.

Results:

Based on the average of the five models, the order of makeup removal efficacy is the following:

Composition from Example 4>Composition from Example 3>Composition from Example 2>Composition from Example 1.

These examples clearly show that jojoba oil has good makeup removing properties, in particular that are greater than other plant oils such as olive oil.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising:
   an aqueous phase comprising 0.5-15 wt. % of a polyol, based on a total weight of the composition;
   from 35 to 90 wt. % of jojoba oil, based on the total weight of the composition; and
   at least one sucrose fatty acid ester.

2. The composition according to claim 1, wherein the sucrose fatty acid ester is chosen from esters derived from the reaction of sucrose(s) and fatty acid(s) comprising from 10 to 24 carbon atoms.

3. The composition according to claim 1, wherein the fatty acid is chosen from oleic acid, lauric acid, palmitic acid, myristic acid, stearic acid, linoleic acid, capric acid and mixtures thereof.

4. The composition according to claim 1, wherein the sucrose fatty acid ester is chosen from esters derived from the reaction of sucrose and of fatty acid comprising from 12 to 18 carbon atoms.

5. The composition according to claim 1, wherein the sucrose fatty acid ester is chosen from sucrose laurate, sucrose palmitate and a mixture thereof.

6. The composition according to claim 1, wherein the sucrose fatty acid ester is chosen from sucrose fatty acid monoesters, diesters, triesters, and mixtures thereof.

7. The composition according to claim 1, wherein the amount of sucrose fatty acid ester(s) present is 0.1 to 20% by weight, relative to the total weight of the composition.

8. The composition according to claim 1, wherein the sucrose fatty acid ester or esters constitute the main surfactant system of the composition.

9. The composition according to claim 1, wherein the sucrose fatty acid ester or esters constitute the only surfactant system of the composition.

10. The composition according to claim 1, wherein it comprises water in an amount less than or equal to 20% by weight relative to the total weight of the composition.

11. The composition according to claim 1, wherein the jojoba oil is present in an amount greater than or equal to 40% by weight relative to the total weight of the composition.

12. The composition according to claim 1, wherein the jojoba oil is present in an amount of at least 50% by weight relative to the total weight of the oily phase of the composition.

13. The composition according to claim 1, wherein said composition comprises less than 5% of mineral oils.

14. The composition according to claim 1, wherein the jojoba oil is present in an amount greater than or equal to 70% by weight relative to the total weight of the composition.

15. The composition according to claim 1, wherein said composition is in gelled form.

16. The composition according to claim 15, wherein the gel has a viscosity of 5 to 190 poise.

17. A method for removing makeup from the skin and/or the eye area and/or the lips comprising applying the composition according to claim 1 to areas of the skin and/or the eyes and/or the lips comprising makeup.

18. A method comprising applying the composition according to claim 1 to a keratin material.

19. A method comprising applying the composition according to claim 15 to a keratin material.

20. The composition according to claim 1, wherein the jojoba oil is present in an amount of greater than or equal to 45 wt. %, based on the total weight of the composition.

21. The composition according to claim 1, wherein the jojoba oil is present in an amount of greater than or equal to 60 wt. %, based on the total weight of the composition.

22. A composition comprising:
an aqueous phase comprising 0-15 wt. % of a polyol, based on a total weight of the composition;
from 35 to 90 wt. % of jojoba oil, based on the total weight of the composition; and
at least one sucrose fatty acid ester,
wherein the aqueous phase comprises 1-10 wt. % of the polyol.

23. The composition according to claim 1, wherein the aqueous phase comprises 0.5-20 wt. % of water.

24. A composition comprising:
an aqueous phase comprising 0-15 wt. % of a polyol, based on a total weight of the composition;
from 35 to 90 wt. % of jojoba oil, based on the total weight of the composition; and
at least one sucrose fatty acid ester,
wherein the sucrose fatty acid ester constitutes the only surfactant system of the composition, with the proviso that the composition does not comprise any other surfactant system.

25. The composition according to claim 1, wherein the jojoba oil is present in an amount of from 35 to 76% by weight relative to the total weight of the composition.

* * * * *